United States Patent [19]

Sugimura

[11] Patent Number: 5,252,821

[45] Date of Patent: Oct. 12, 1993

[54] TOY STICK MECHANISM WITH AN OPTICAL SYSTEM

[75] Inventor: Masahiro Sugimura, Aichi, Japan

[73] Assignee: Nidek Co., Ltd., Gamagori, Japan

[21] Appl. No.: 910,060

[22] Filed: Jul. 8, 1992

[30] Foreign Application Priority Data

Jul. 31, 1991 [JP] Japan .................. 3-215817

[51] Int. Cl.⁵ .................. G01V 9/02; G09G 3/02
[52] U.S. Cl. .................. 250/22; 200/6 A; 250/229; 345/161
[58] Field of Search ............ 250/229, 221, 231.1, 250/231.19; 340/709; 200/6 A

[56] References Cited

U.S. PATENT DOCUMENTS

| | | | |
|---|---|---|---|
| 4,382,166 | 5/1983 | Kim | 340/709 |
| 4,489,303 | 12/1984 | Martin | 200/6 A |
| 4,533,827 | 8/1985 | Fincher | 250/221 |
| 4,584,510 | 4/1986 | Hollow | 250/229 |
| 4,616,115 | 10/1986 | Potyka | 200/6 A |
| 4,748,323 | 5/1988 | Holiday | 250/229 |
| 4,794,388 | 12/1988 | Matthews | 340/709 |
| 4,879,556 | 11/1989 | Duimel | 340/709 |
| 5,008,534 | 4/1991 | Yonezawa et al. | 250/229 |
| 5,113,179 | 5/1992 | Scott-Jackson et al. | 200/6 A |

FOREIGN PATENT DOCUMENTS 2-88028 3/1990 Japan .
2-88029 3/1990 Japan .
3-1689  1/1991 Japan .

*Primary Examiner*—David C. Nelms
*Assistant Examiner*—Michael Messinger
*Attorney, Agent, or Firm*—Nikaido, Marmelstein, Murray & Oram

[57] ABSTRACT

The present invention provides a joy stick mechanism having a simplified structure in which a size reduction of the apparatus can be attained, there is little possibility of breaking of electric wires, and switching can be surely realized. To this end, the joy stick mechanism is arranged in such a manner that it includes an optical system such as a slit lamp laser delivery system or a fundus camera and the optical system can be moved fore and aft, and right and left by operating a joy stick, the mechanism being provided with switch button device located at a top portion of the joy stick bar, a movable shaft which can move in an axial direction of the joy stick bar by the movement of the switch button device, a detection device for detecting the movement of the shaft, and a control device for generating a trigger signal of photographing, coagulating and so forth on the basis of the detected result.

4 Claims, 2 Drawing Sheets

TOY STICK MECHANISM WITH AN OPTICAL SYSTEM

DETAILED DESCRIPTION OF THE INVENTION

1. Industrial Field of the Invention

The present invention relates to a joy stick mechanism for moving an optical system such as a slit lamp laser delivery system or a fundus camera, particularly, an optical system of an ophthalmic apparatus fore and aft, and right and left so as to adjust the optical system with an eye to be examined, and for operating the switching of the photographing or coagulation apparatus.

2. Related Art

There are known various joy stick mechanisms. The joy stick mechanism may coarsely and finely move an optical system such as a slit lamp laser delivery system or a fundus camera fore and aft, and right and left, by shifting an operation bar, i.e., a joy stick bar. Some of the joy stick mechanisms are each provided with a device for vertically moving the optical system by rotating an outer periphery of the joy stick bar. Further, as is known, some joy sticks are provided with switching means for photographing or conducting remedy.

Various measures have been proposed for giving a switching function to the joy stick mechanism. The applicant of this invention has proposed one measure in Japanese Patent Examined Publication No. 3-1689. In this published specification, there are provided a shaft capable of rotation and inclination (revolution), the shaft being disposed on the central axis of a joy stick bar, a rotary knob for an operator to rotate with his fingers which rotary knob is disposed at an outer peripheral upper portion of the shaft, an operation button located at a top portion of the rotary knob, a revolving knob disposed below the rotary knob and on the outer periphery of the shaft, which revolving knob is arranged not to be influenced by the rotation of the rotary knob, and a switch located inside of the revolving knob. Also, the operation button includes a connection rod secured thereto which is provided with a ring-like plate for engagement with the switch.

Further, as seen in Japanese Patent Unexamined Publication Nos. 2-88028 and 2-88029, there have been proposed a switching mechanism by means of a magnetic core and a coil provided on an outer periphery of a joy stick bar, and a switching mechanism by means of a coil utilizing electromagnetic induction.

The joy stick mechanism proposed by the applicant is excellent in operatability, but it has a rather complicated structure. Also, since the switch and electric wires are positioned within the joy stick, the wires may unfavorably be tugged so as to be broken in accordance with the inclination (revolution) of the joy stick bar.

Each of the above-described mechanisms including the switching function by means of the coils has disadvantages that the apparatus is increased in size because of needing large-sized coils, and that the durability of the mechanism is not satisfactory because the coils are moved by the inclination of the joy stick bar.

SUMMARY OF THE INVENTION

In view of the above-mentioned disadvantages, the present invention aims to provide a joy stick mechanism with a simplified structure in which a size reduction of the apparatus can be realized, there is little possibility of breaking of electric wires, and switching can be surely performed.

In order to attain the above object, the joy stick mechanism according to the invention possesses such characteristics as to be described below.

As a first feature of the invention, there is provided a joy stick mechanism with an optical system such as a slit lamp laser delivery system or a fundus camera for finely moving the same fore and aft, and right and left by operating a joy stick bar, the mechanism comprises switch button means located at a top portion of the joy stick bar, a movable shaft which can move in an axial direction of the joy stick bar by the movement of the switch button, detection means for detecting the movement of the movable shaft, and control means for generating a trigger signal of photographing, coagulating and so forth on the basis of the detected result.

As a second feature of the invention, a rotary knob is provided on an outer periphery of the joy stick bar, in order to vertically move the optical system.

As a third feature of the invention, the above-mentioned detection means is photo-detection means arranged so as to move in a body with a slidable board for coarse adjustment.

As a fourth feature of the invention, the photo-detection means is preferably a photo-interrupter.

As a fifth feature of the invention, in the joy stick mechanism using the photo-interrupter, it is also preferable that a size of the lower end surface of the movable shaft is formed to be enough large to be optically detected in association with a photo-detecting surface.

As a sixth feature of the invention, in the above joy stick mechanism, it is further desirable that the lower end surface of the movable shaft is formed in a concave shape.

As a seventh feature of the invention, it is more favorable that the detection means of the joy stick mechanism according to the above first feature is a Hall element for detecting a quantity of magnetism of a magnetic member provided on the movable shaft, the Hall element being arranged to move in a body with the slidable board for coarse adjustment.

DETAILED DESCRIPTION OF THE PREFERRED EMBODIMENTS

Figure 1:
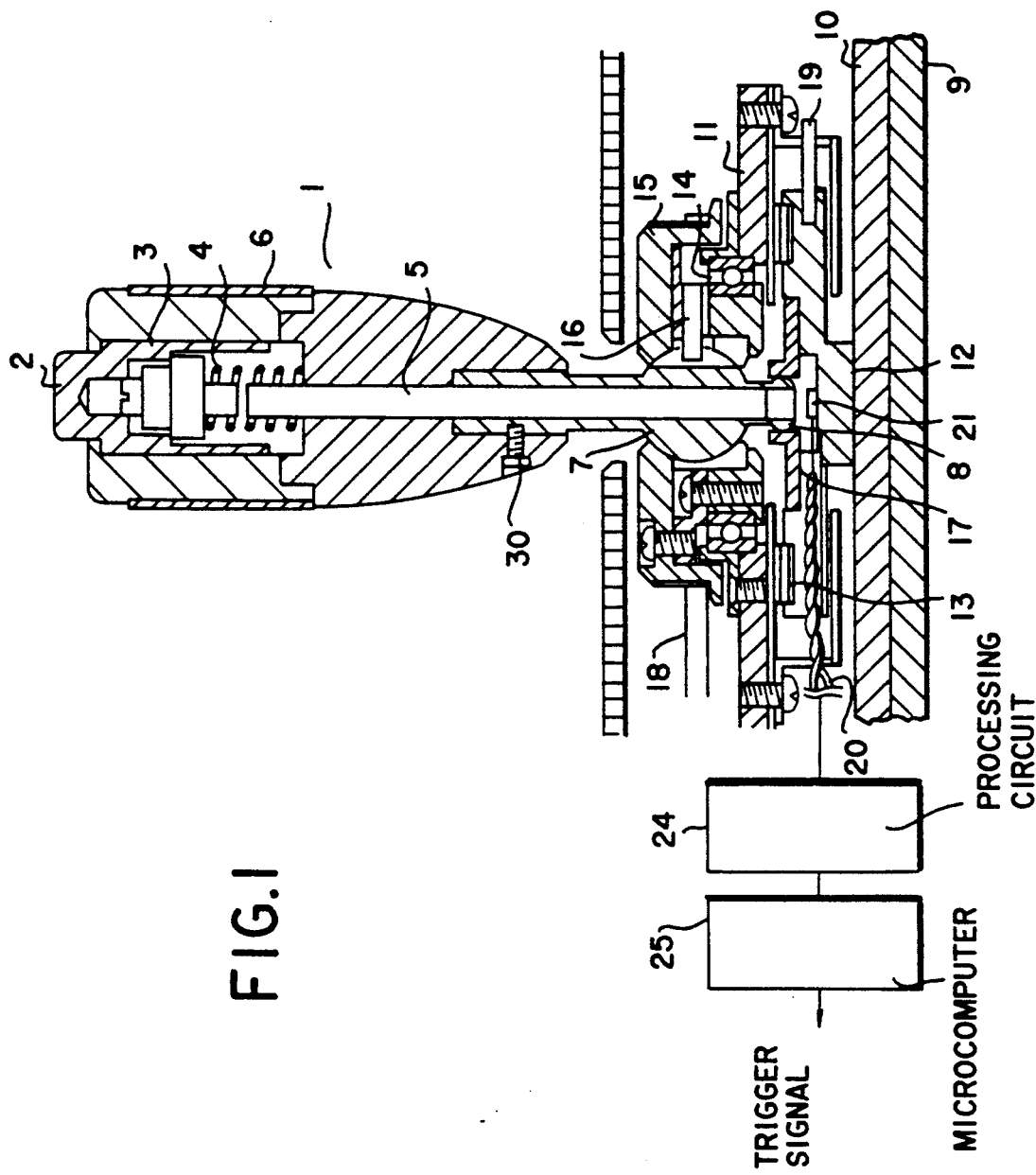
FIG. 1 is a sectional view illustrative of a joy stick mechanism according to a first embodiment of the present invention.

Preferred embodiments of the invention will be described hereinafter with reference to the drawings. FIG. 1 is a sectional view showing a joy stick mechanism according to a first embodiment of the invention.

Reference numeral 1 designates a joy stick bar (operation bar) which includes a push button 2 located at the top portion. The button 2 is pushed up at its flange portion 3 by means of a spring 4. A movable shaft 5 is located below the button 2, the shaft 5 being positioned coaxially with the joy stick bar 1 and axially extending through the joy stick bar 1. The shaft 5 is arranged axially movable when the button 2 is pushed downwardly with a finger. The joy stick bar 1 is provided with a knob 6. The joy stick bar 1 also includes a first spherical portion 7 and a second spherical portions 8 having substantially spherical shape at the lower portions, the both spherical portions respectively having through-holes. The shaft 5 extends through the holes in movable condition. The knob 6 is in a body with the first spherical portion 7 by means of a setscrew 30 so as to rotate around the shaft 5 with the first spherical portion. Meanwhile, it is preferable for the joy stick bar 1 to be moved and inclined in every direction at an angle of about 15 degrees with respect to the vertical axis of the joy stick mechanism (in this embodiment, the axis of the joy stick bar 1 is deviated from its original position by a distance of about 1 mm when it is inclined at 15 degrees). In this connection, it is necessary that a lower end of the movable shaft 5 is sufficiently large in size to be detected with respect to a photo-detecting surface of a photo-interrupter which will be described below, or it is necessary that a shape at the lower end of the movable shaft 5 and material for manufacturing the same is appropriately chosen so that the movement of the shaft 5 can be detected even if the joy stick bar 1 inclines (for example, the lower end is formed to have a concave spherical surface or a scattering surface).

Reference 9 denotes a supporting structure, and reference 10 denotes a friction plate adhered on the supporting structure 9. Numeral 11 is a base plate on which an optical system such as a slit lamp laser delivery system or a fundus camera is mounted via a vertical movement mechanism (not shown). The base plate 11 is movable on the friction plate 10 in a horizontal direction fore and aft, and right and left with a slidable board 12 being interposed between the base plate 11 and the friction plate 10. Reference 13 indicates a sliding plate provided between the slidable board 12 and the base plate 11.

Numeral 14 shows ball bearing. A housing 15 is located on the base plate 11 in a rotatable manner via the ball bearing 14. The first spherical portion 7 of the joy stick bar 1 is rotatably retained within the housing 15. A key 16 fixedly attached to the housing 15 engages with a groove of the first spherical portion 7. When the optical system is adjusted finely, the second spherical portion 8 of the joy stick bar 1 rotates along a contact surface of a movement control plate 17 formed integrally with the slidable board 12. Numeral 18 is a timing belt for transmission of rotation of the housing 15 to the vertical movement mechanism. Numeral 19 is a key supported by the slidable board 12 and loosely fitted to the base plate 11 for preventing the slidable board 12 from rotation. Numeral 20 indicates electric wires held on the slidable board 12.

Reference 21 designates a photo-interrupter for detecting a location of an end face of the movable shaft 5, the photo-interrupter being secured to the slidable board 12. The photo-interrupter 21 typically comprises infrared LED and a phototransistor, such as, and, for example, such a kind of "PG-101 (manufactured by Hikari Denshi Kogyo Kenkyujo)" is suitable for using. When the button 2 is pushed and the lower end of the movable shaft 5 comes near the photo-interrupter so as to reach a position at a certain distance (about 1 mm in this embodiment) apart from the photo-interrupter, a processing circuit 24 judges that the condition means ON and supplies a signal to be input into a microcomputer 25.

An operation of the joy stick mechanism having the above-mentioned structure will be explained in detail.

An operator manipulates the joy stick bar 1 fore and aft, and right and left so as to glidingly move the slidable board 12 on the friction plate 10, thereby making coarse adjustment of the optical system mounted on the base plate 11 with respect to the eye to be examined. Then, when the rotary knob 6 of the joy stick bar 1 is rotated around its own rotational axis for rotating the first spherical portion 7, the housing 15 is rotated by the key 16 engaging with the groove of the first spherical portion 7. The timing belt 18 is actuated by the rotation of the housing 15, so that the vertical movement mechanism (not shown) is driven for carrying out the vertical adjustment between the eye to be examined and the optical system.

Subsequently, the joy stick bar 1 is inclined in order to finely shift the optical system in the horizontal direction for adjustment of the optical system with respect to the eye to be examined. Frictional resistance between the slidable board 12 and the sliding plate 13 is smaller than the resistance between the slidable board 12 and the friction plate 10. Therefore, when force is applied to the joy stick bar 1 for inclination, the base plate 11 slides over the slidable board 12 under such a condition that the slidable board 12 stationarily rests on the friction plate 10. As a result, the joy stick bar 1 rotates around the second spherical portion 8 while being inclined, to finely move the optical system mounted on the slidable board 12.

After the alignment between the eye to be examined and the optical system is completed and preparations are made for photographing or measuring, the button 2 is pushed to be lowered against the spring 4 so that the lower end of the button 2 presses the movable shaft 5 downwardly in the axial direction. The location of the lower end of the axially moved shaft 5 is detected by means of the photo-interrupter 21. When a signal from the photo-interrupter 21 is processed by the processing circuit 24 and the photo-interrupter 21 detects that the lower end of the movable shaft 5 comes near and reaches a location at a certain distance from the photo-interrupter 21, the processing circuit 24 supplies an "ON" signal to the microcomputer 25, and the microcomputer 25 then sends a trigger signal of photographing, measuring or coagulating.

Figure 2:
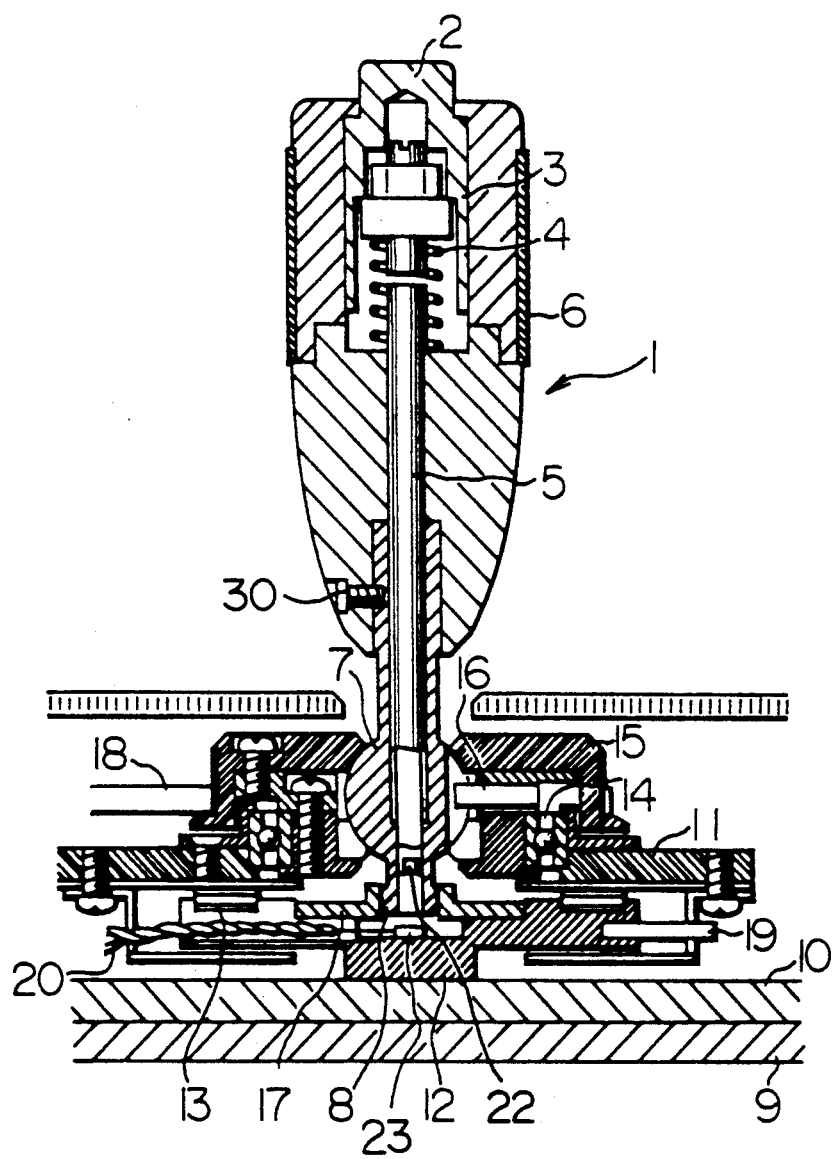
FIG. 2 is a sectional view illustrative of a joy stick mechanism according to a second embodiment of the invention.

FIG. 2 is a sectional view showing a second embodiment according to the invention. This embodiment is similar to the first embodiment, except that a magnet 22 is secured at the lower end of the movable shaft 5 and that a Hall element 23 is provided in place of the photo-interrupter 21. As the Hall element 23 converts magnetism into electricity, a voltage is generated in the Hall element 23 when the push button 2 is depressed for forcing the magnet 22 to approach the Hall element 23. Accordingly, switching can be realized by sending this signal to a microcomputer which is not illustrated in FIG. 2.

The above description is made as for the joy stick mechanism having the photo-interrupter or the Hall element for switching means. The switching means may be modified in various ways to miniaturize the apparatus.

The revolving or rotating mechanism of the joy stick bar is not restricted to the above-described ones. It is needless to say that various modifications of the mechanism can be included in the present invention and the skilled persons can modify or vary the embodiment without departing from a spirit of the invention.

According to the joy stick mechanism of the invention, a structural simplification and a size reduction of the apparatus can be realized. Also, there is little possibility of breaking of the electric wires and switching can be surely performed.

What is claimed is:

1. A joy stick mechanism for alignment of an ophthalmic apparatus with an eye to be examined, said joy stick mechanism comprising:
   a) moving means for moving an optical system of said ophthalmic apparatus on a horizontal plane and in a vertical direction, said moving means including
      i) a supporting structure having friction resistance on an upper surface thereof;
      ii) a base plate mounting said ophthalmic apparatus and moving by a slidable board sliding against said supporting structure;
      iii) a sliding plate provided between the slidable board and the base plate for adjusting friction therebetween and for helping the base plate sliding against the slidable board;
      iv) a joy stick bar provided with first and second spherical portions at lower portions thereof, said first spherical portion being rotatably held by said base plate; and
      v) transferring means for transferring a rotational force of said joy stick bar through said first spherical portion to a vertically moving mechanism of the optical system of the ophthalmic apparatus; said joy stick mechanism further comprising
   b) switching means for switching in a non-contacting manner, said switching means including
      i) switch button means located at a top portion of the joy stick bar, said switch button means for initiating a generation of a trigger signal;
      ii) a movable shaft positioned coaxially with the joy stick bar, said movable shaft being movable in an axial direction of said joy stick bar by a movement of the switch button means; and
      iii) detecting means located on said slidable plate for detecting the movement of said movable shaft; said joy stick mechanism also comprising
   c) input means for inputting a detected result from said detecting means to signal generating means in said ophthalmic apparatus, thereby generating the trigger signal.

2. A joy stick mechanism according to claim 1, wherein said detecting means comprises a photo-interrupter, said photo-interrupter detecting a reflected light from a bottom surface of said movable shaft.

3. A joy stick mechanism according to claim 2, wherein said bottom surface of said movable shaft is formed as a concave surface.

4. A joy stick mechanism according to claim 1, wherein said detecting means is a Hall element for detecting a quantity of magnetism of a magnetic member provided on said movable shaft.

* * * * *